United States Patent [19]

Miethe et al.

[11] Patent Number: 5,017,476

[45] Date of Patent: May 21, 1991

[54] METHOD FOR THE BIOCATALYTIC REACTION OF ORGANIC SUBSTANCES

[75] Inventors: Peter Miethe, Halle; Harald Voss, Halle-Neustadt; Ronald Gruber, Halle, all of German Democratic Rep.

[73] Assignee: Degussa Aktiengesellschaft, Frankfurt, Fed. Rep. of Germany

[21] Appl. No.: 350,364

[22] Filed: May 8, 1989

[30] Foreign Application Priority Data

May 6, 1988 [DD] German Democratic Rep. ................................. 3154774

[51] Int. Cl.$^5$ ............... C12P 33/02; C12P 7/24; C12P 7/64; C12N 11/14
[52] U.S. Cl. ..................... 435/61; 435/147; 435/176; 435/134; 435/135; 435/174; 435/156; 435/123; 435/52; 435/41; 435/171
[58] Field of Search ............... 435/176, 134, 135, 174, 435/147, 156, 61, 123, 52, 41, 171

[56] References Cited

U.S. PATENT DOCUMENTS

| | | | |
|---|---|---|---|
| 4,268,527 | 5/1981 | Matsuo et al. | 435/134 |
| 4,348,476 | 9/1982 | Hou | 435/123 |
| 4,503,153 | 3/1985 | Geigert et al. | 435/147 |
| 4,818,695 | 4/1989 | Eigtved | 435/134 |
| 4,839,287 | 6/1989 | Holmberg et al. | 435/134 |

FOREIGN PATENT DOCUMENTS

| | | | |
|---|---|---|---|
| 0068594 | 1/1983 | European Pat. Off. | 435/182 |
| 0120285 | 10/1984 | European Pat. Off. | 435/134 |
| 59-28482 | 2/1984 | Japan . | |
| 0637789 | 6/1986 | Japan | 435/134 |
| 62-278988 | 6/1987 | Japan . | |
| 2168344 | 6/1986 | United Kingdom | 435/156 |

OTHER PUBLICATIONS

Kirk-Othmer reference, Liquid Crystals, vol. 14; pp. 395-425.

*Primary Examiner*—Douglas W. Robinson
*Assistant Examiner*—Michael V. Meller
*Attorney, Agent, or Firm*—Cushman, Darby and Cushman

[57] ABSTRACT

A biocatalytic method for reacting organic, especially poorly water-soluble substances. Enzymes, prokariotic and eukariotic cells or combinations of enzymes and cells are immobilized in lyotropic liquid crystals (mesophases), preferably with inverse phase structure. The supply of substrate and the removal of product are performed via one or more solvent phases. Organic solvents function as solvent phases. In addition, an aqueous solvent phase can also be present. In order to produce these two and three-phase systems, three-component systems consisting of water, organic solvent and surfactant are used.

7 Claims, No Drawings

METHOD FOR THE BIOCATALYTIC REACTION OF ORGANIC SUBSTANCES

The present invention relates to a method for the biocatalytic reaction or conversion of organic substances.

BACKGROUND OF THE INVENTION

Biocatalytic reactions are currently primarily performed in systems which are aqueous or at least contain a considerable amount of water. This mode of procedure is disadvantageous if hydrophobic substrates which are poorly water-soluble or non-water-soluble, e.g. steroids, lipids, hydrocarbons, long-chain aliphatic or aromatic alcohols, aldehydes or carboxylic acids, are to be reacted by biocatalysis or if an enzyme-catalyzed synthesis is to be performed as a reversal of a hydrolysis reaction. In addition, enzymes themselves can also be strongly hydrophobic. In aqueous systems, this can cause agglomeration and, consequently, a loss of biocatalytic activity.

The procedures known and employed in the past for the biocatalytic reaction of hydrophobic substrates are:
1. The use of enzymes in organic solvents or water-containing solvent mixtures.
2. The use of two-phase and multiphase systems.
3. The use of one-phase, surfactant-containing systems, especially of reverse micellar phases.

In systems of Type 1, there is a danger of enzyme denaturation. This can only be retarded by means of the selection of suitable solvents and by enzyme immobilization. The residence times of the catalysts are therefore only low. The use of microorganisms and other cells as biocatalysts is possible only to a limited extent.

There is also the danger, in liquid systems of Type 2, of denaturation at the phase boundary. Moreover, the reaction speed is low due to the low substrate concentration in the aqueous phase. An advantageous variant of Type 2 is the use of hydrophilic polymer gels for enzyme inclusion. These polymer gels, e.g. based on gelatin, agar or alginate, can also be used in organic solvents. However, the concentration of the hydrophobic substrate in the gel is low because of the hydrophilic character of the polymer gel. The result is a low conversion rate in biocatalysis.

Systems of Type 3 exhibit more advantageous properties. Reverse micelles are globular surfactant aggregates which can be formed by surfactants in organic solvents, e.g. hexane, heptane, cyclohexane, benzene or dodecanol in the presence of slight amounts of water.

The water forms a "waterpool" inside the micelle in which enzymes can be included or solubilized. It has been demonstrated frequently that the enzyme activity can be maintained by this means for a considerable time. In addition, it is known that microorganisms, e.g. *E. coli* or *B. subtilis*, can maintain a part of their enzyme activity in such phases. Hydrophobic substrates can generally be introduced directly into the organic solvent in the case of reverse micellar systems.

However, preparative steps for retaining the surfactant aggregates and for separating the products are necessary in the processing mode, which imposes considerable expense. An improvement is possible in a continuous processing mode using immobilized reverse micelles. A hollow fiber membrane system has been suggested for this purpose. These membranes add significant expense, are often not resistant to solvents, tend to become clogged and represent a considerable flow resistance, so that the process must be carried out under pressure.

In general, it must be concluded that one-phase, surfactant-containing systems are extremely unreliable for industrial biocatalysis since, in particular, the problems of a simple separation of the product, of the removal of surfactant impurities from the product and of the continuous processing mode remain as yet unsolved.

SUMMARY OF THE INVENTION

The object of the present invention is to react organic substances in a continuous or discontinuous process in the presence of a lyotropic mesophase containing a biocatalyst, while avoiding injury to the biocatalyst and with a simple separation of a product which is free of surfactant or contains only a small amount of surfactant.

According to the present invention, biocatalysts immobilized in lyotropic mesophases are used for reacting organic substances either in a two-phase region of a two-component mixture consisting of lyotropic mesophase and organic solvent or in a three-phase region of a three-component mixture consisting of water, an organic solvent or mixture of organic solvents and a surfactant or mixture of surfactants.

In the two-phase region, consisting of lyotropic mesophase and organic solvent, the supplying of substrate and the removal of product take place via the organic solvent phase; in the three-phase region, consisting of lyotropic mesophase, organic solvent and water, the supplying of substrate takes place via the solvent phase and the removal of product via the aqueous phase or vice versa, in which instance product and substrate must then be correspondingly water-soluble.

In addition, substrates can be added in solid form in the two-phase region and dissolved directly in the mesophase. Substrates can also be supplied as gas and/or be removed as gas.

A method which is especially advantageous on an industrial scale consists of charging a porous carrier material such as glass sintered bodies and ceramic sintered bodies with lyotropic mesophase. Such a catalytic system can be generated e.g. by melting the phase, in which instance the biocatalytically active mesophase re-forms in the pores after cooling off.

Hydrophobic solvents such as hexane, heptane, octane, cyclohexane, decanol, butyl acetate, diethyl ether or solvent mixtures such as hexane/acetone, hexane/butanol can be used as organic solvents.

The following can be used as surfactants: Anionic surfactants such as alkali alkyl sulfates, alkali dialkyl sulfosuccinates, alkaline earth dialkyl sulfosuccinates, or cationic surfactants such as alkyl ammonium salts, alkyl pyridinium salts, alkyl trimethyl ammonium salts or zwitterionic surfactants such as phospholipids, sulfobetaines, carbobetaines or non-ionic surfactants such as polyoxyethylene ether, polyoxyethylene ester, polyoxyethylene sorbitan ester, alkyl phenol polyethylene glycol ether, corresponding polyoxypropylene derivatives or copolyoxyethylene polyoxypropylene derivatives or corresponding surfactant mixtures.

In addition to isolated enzymes such as alcohol dehydrogenase, chymotrypsin and lipase, optionally together with a coenzyme such as NAD/NADH, prokariotic and eukariotic cells, e.g. from *E. coli* or *Saccharomyces cerevisiae*, or co-immobilized enzymes and cells can also be used as biocatalysts, optionally together with a coenzyme such as NAD/NADH. It was found that both cubic, cubically bicontinuous, hexagonal as well as lamellar, lyotropic mesophases are suitable for solubilizing biocatalysts. The greatest biocatalytic activity is achieved when using inverse phases. Both cells as well as isolated enzymes exhibit high activity in a multiphase system consisting of mesophase and one or more solvent phases. It was surprisingly found, in the multiphase system used in accordance with the invention, that the biocatalytic activity decreases only slightly in contrast to a normal, two-phase, liquid system even after rather long storage times and reactor residence times, that only very slight diffusion resistances appear and that the solvent phase contains only extremely little surfactant, which makes it possible to separate out an almost surfactant-free synthetic product.

The method of the invention can be used with advantage e.g. in the reaction of organic substances such as steroids, lipids, hydrocarbons, long-chain aliphatic and aromatic alcohols, aldehydes, carboxylic acids, esters, amino acids and peptides. The use of biocatalysts for such syntheses is rendered possible in a considerably simplified and more economical manner in particular in the presence of hydrophobic substrates and products. The biocatalysis is influenced by the particular coefficients of distribution of the components in the phases and can be controlled via the HLB value (hydrophilic-lipophilic balance).

It is readily possible, when using suitable, simple reaction apparatus, to retain the liquid-crystalline system containing biocatalyst with the aid of mechanical retention devices, e.g. settlers, separator lamellae, baffles or filters.

Further information on the nature of a mesophase may be found in an article in Kirk-Othmer. Encylopedia of Chemical Technology, Vol 14, pages 395–426

DETAILED DESCRIPTION OF PREFERRED EMBODIMENTS

The invention will now be illustrated in more detail in the following examples.

EXAMPLE 1

136 ml of a 10% by weight solution of tetraethylene glycol dodecyl ether in hexane are combined with 10 ml of a 21 mM aqueous NAD solution and agitated. 5 ml of an aqueous solution of yeast alcohol dehydrogenase and sodium chloride are injected into this system, which appears cloudy at first. The salt concentration is 0.1 mole/l and the enzyme concentration 0.5 g/l. After brief agitation, a two-phase system results therefrom which consists of a clear, viscous, lyotropic mesophase and of pure hexane. Any amounts of hexane desired can be added to the system. A system which can be readily manipulated is produced upon the addition of 600 ml hexane. Approximately 15 ml ethanol are sprayed in as substrate in a batch method. The enzymatic oxidation to the acetaldehyde takes place with formation of NADH. The latter can be demonstrated spectrophotometrically at a wavelength of 365 nm in the mesophase. The system still exhibits 80% of the initial activity even after a storage time of two months at room temperature.

If 2 ml cinnamaldehyde are added as a second substrate, it is reduced to cynnamyl alcohol with consumption of the NADH formed.

The preparation of cynnamyl alcohol is possible in this manner, which can be readily separated from the hexane phase, e.g. by extracting with water or steam distillation.

EXAMPLE 2

The same procedure is used as in Example 1. Instead of the 5 ml aqueous enzyme solution, a suspension of Saccharomyces cerevisiae with a concentration of 10 g/l (relative to dry mass) is added to the system. The spectroscopic testing for the NADH formed and the product workup can be performed in a manner analogous to that described in Example 1.

EXAMPLE 3

130 ml of a 10% by weight solution of tetraethylene glycol dodecyl ether in hexane are combined with 10 ml of a 21 mM aqueous NAD solution and subsequently 5 ml of an aqueous solution of yeast alcohol dehydrogenase are added in a manner analogous to Example 1. Another 80 ml water are added, then the mixture is centrifuged. 3 phases are separated, the hexane phase, the lyotropic mesophase and a water phase. The lyotropic mesophase contains the added enzyme. Now, approximately 10 ml ethanol and 2 ml cinnamaldehyde can be added into the hexane phase in a manner analogous to that in Example 1. After approximately 20 minutes, cynnamyl alcohol can be demonstrated spectroscopically in the water phase at=245 nm.

EXAMPLE 4

136 ml of a 10% by weight solution of tetraethylene glycol dodecyl ether in hexane are combined with 15 ml of an aqueous suspension of Aspergillus glaucus. The concentration of the suspension is in a range of 5-8 g/l (relative to dry mass). After agitation and centrifugation, a two-phase system is produced which consists of a clear, lyotropic mesophase and hexane. Then, 5 ml cinnamaldehyde are added. Tyrosine can be demonstrated in the presence of ammonium ions after 3 hours residence time in the hexane supernatant. The presence of this material can be demonstrated with thin-layer chromatography on a silica gel plate, butanol/acetic acid/ water=4/1/1 as mobile solvent.

EXAMPLE 5

Another two-phase system, in which lyotropic mesophase and organic solvent coexist and in which biocatalyses can be performed in the manner described in Examples 1 and 2, can be prepared in the following manner: A 5% by weight solution of polyoxyethylene sorbitan trioleate (Tween 85) is prepared in heptane. 1.4 ml of this solution are combined with 800 $\mu$l of an aqueous solution or an aqueous suspension of cells and agitated. A clear, highly viscous, lyotropic mesophase is produced which is in equilibrium with pure heptane.

EXAMPLE 6

500 ml of a 10% by weight solution of Präwozell (a mixture of various alkylphenol ethoxylates, Chemische Werke Buna) in hexane are combined with 40 ml of a 75 $\mu$M aqueous NADM solution and agitated. 10 ml of a $10^{-8}$M aqueous solution of horse liver alcohol dehydrogenase (SERVA) and $0.5 \cdot 10^{-7}$M formate dehydrogenase (SERVA) are injected into this three-phase system, which is cloudy at first. After a brief agitation, a two-phase system is produced consisting of lyotropic mesophase and hexane. If 100 $\mu$l of a prochiral compound of the type $CH_3-(CH_2)_n-CO-CH_2-COOCH_3$; n=1-7 are dissolved as substrate in the hexane phase, the corresponding $\beta$-hydroxy compounds can be demonstrated after approximately 10 to 20 minutes, with gas chromatography. The reduction takes place stereospecifically and an enantiomer excess of the R form of 90 to 97% is achieved. A regeneration of the NADH consumed can be achieved by the addition of 200 $\mu$l formic acid. Up to 200 reaction cycles are possible with the system. In addition, a continuous processing mode in a mixer-settler system or in a membrane reactor is also possible.

EXAMPLE 7

50 ml of a suspension of *Arthrobacter simplex* in a phosphate buffer (1/15M, pH 7.0) are added to 5 ml of a 10% solution of Präwozell (a mixture of various alkylphenol ethoxylates, Chemische Werke Buna) in hexane. After agitation, a mesophase and supernatant hexane result. The latter is poured off and 250 ml of a solvent mixture consisting of 1 part by volume toluene and 4 parts by volume hexane, which contains 1 mg/ml progesterone, are added. The system is agitated at 20° C. at 500 rpms. After 10 hours, 1-dehydroprogesterone can be demonstrated in the supernatant. The evidence of this material can be obtained with thin-layer or gas chromatography.

EXAMPLE 8

A two-phase system is prepared in a manner analogous with Example 7. Instead of the aqueous enzyme and cofactor solution, 50 ml of a suspension of Pseudomonas E3 with a concentration of 20 mg/ml (relative to the mass of moist cells) is added. The system is flushed continuously at 40° C. with a propene/air mixture. The escaping gas is conducted through a cold trap containing carbon tetrachloride. After approximately 2 hours, propylene oxide can be demonstrated in the carbon tetrachloride with ga chromatography.

What is claimed is:

1. A method for the biocatalytic reaction of organic substances which comprises immobilizing a biocatalyst in a lyotropic mesophase in a two-phase region of a two-component mixture consisting of lyotropic mesophase and organic solvent, supplying at lest one substrate and removing at least one product in the two-phase region wherein the supplying of substrate and the removal of product taking place via the organic solvent phase in said two phase system.

2. A method according to claim 1 in which a lyotropic mesophase with inverse phase structure is used for solubilizing the biocatalyst.

3. A method according to claim 1 in which the biocatalyst is selected from the group consisting of enzymes, prokariotic and eukariotic cells or enzymes in combination with cells.

4. A method according to claim 1, in which a porous carrier material is charged with lyotropic mesophase containing biocatalyst and is used in this form.

5. A method according to claim 1 in which the substrate is added in the two-phase region in solid form and is dissolved directly in the mesophase.

6. A method according to claim 1 in which the substrate is supplied as gas and/or the product is removed as gas.

7. A method for the biocatalytic reaction of organic substances which comprises immobilizing a biocatalyst in a lyotropic mesophase in a three-phase region of a three-component mixture consisting of water, an organic solvent or mixture of organic solvents and a surfactant or mixture of surfactants, wherein the supplying of substrate takes place via the solvent phase and the removal of product via the aqueous phase or vice versa in which instance the product and substrate must then be corresponding water-soluble and soluble in the organic phase or vice versa, or the substrate or the product being in solid or gaseous form.

* * * * *